United States Patent [19]

Chikindas et al.

[11] Patent Number: 5,672,351

[45] Date of Patent: Sep. 30, 1997

[54] ANTI-MICROBIAL COMPOSITIONS

[75] Inventors: Michael C. L. Chikindas, Bromborough; Andrew Joiner, Liverpool; Philip William Small, Bromborough, all of Great Britain

[73] Assignee: Chesebrough-Pond's USA Co., Division of Conopco, Inc., Greenwich, Conn.

[21] Appl. No.: 570,182

[22] Filed: Dec. 11, 1995

[30] Foreign Application Priority Data

Dec. 12, 1994 [EP] European Pat. Off. ............. 94309258

[51] Int. Cl.$^6$ ................................. A61K 6/00; A61K 7/48
[52] U.S. Cl. ........................ 424/401; 424/49; 424/405; 514/2
[58] Field of Search .................. 424/401, 49, 405; 514/2

[56] References Cited

FOREIGN PATENT DOCUMENTS

| 0 149 254 | 7/1985 | European Pat. Off. . |
| 03 261 717 | 11/1991 | Japan . |
| 04182420 | 6/1992 | Japan . |

OTHER PUBLICATIONS

The Journal of Biological Chemistry, vol. 265, No. 7, Mar. 5, 1990, pp. 3898–3905.
Peptides, 1990, pp. 843–846.

*Primary Examiner*—Jyothsan Venkat
*Attorney, Agent, or Firm*—Milton L. Honig

[57] ABSTRACT

The present invention relates to anti-microbial cosmetic compositions for the care of the human body or parts thereof, comprising derivatives of histatins or fragments thereof. It has been found that the anti-microbial activity of histatins or their fragments can be significantly enhanced by capping them at the C-terminus or at the C- and N-terminus and/or complexing them with anti-microbially-active metal ions. The thus modified histatins and histatin fragments were found to have a significantly increased activity against a range of microbial strains, and were found to be useful as controlled delivery agents for the metal ions. They are suitable for a whole range of anti-microbial applications, such as anti-plaque, and-caries, anti-bad breath oral applications, deodorant applications, personal hygiene applications and so on, for which they are included in any suitable carrier medium. Preferred are the capped derivatives, which have been complexed with Ag, Cu, Zn or Sn.

12 Claims, No Drawings

ANTI-MICROBIAL COMPOSITIONS

BACKGROUND OF THE INVENTION

1. Field of the Invention

The present invention relates cosmetic compositions for the care of the human body or parts thereof, particularly to oral care compositions which comprise particular biomolecules and derivatives thereof as anti-microbial agents. More particularly, it relates to such compositions which comprise biomolecules derived from histatins as anti-microbial agents.

2. The Related Art

Histatins are a group of small, neutral or cationic histidine-rich peptides, present in human parotid and submandibular gland secretions. At present, 12 histatins are known and have been isolated from human saliva. Of these known histatins, the histatins-1, -3 and -5 have received the most attention in the scientific literature.

Histatins-1, -3 and -5 have been described by Oppenheim al. in J. Biol. Chem. 1988, 263 (16), p 7472 and Troxler et al. in J. Dent. Res. 1990, 35 (2), p 137. These publications describe the amino acid sequences of the histatins, and mention the ability of histatins -1, -3 and -5 to kill the pathogenic yeast C. albicans. Histatin 5 was the most effective in this respect.

Mackay et al. in Infect. Immun. 1984, 44, 695 referred to the inhibition of several strains of S. mutans by partially purified mixtures of histatins. These data show, that histatins in parotid and submandibular gland secretions play a major role in the non-immune oral host defence system.

Not unexpectedly, therefore, it has been proposed in JP-A-04/182420 (Sangi KK) to include histatin -1, -3, or particularly -5 in oral care compositions to treat periodontal disorders, the histatins inhibiting the activity of B. gingivalis. However, histatin-5 can actually stimulate the growth of certain plaque bacteria such as S. sanguis, S. salivarius and Actinomyces sp., which limits its usefulness as a broader spectrum anti-microbial agent in oral care compositions.

Raj et al, studied salivary histatin-5 and its dependence of sequence, chain length and helical conformation for candidacidal activity (J. Biol. Chem. 1990, 265 (7), pp 3898–3905). They synthesized histatin-5 and several fragments of histatin-5. They found, that the sequence at the C-terminal of histatin-5 with a minimum chain length of 14 residues and $\alpha$-helical conformation are important structural requirements for appreciable candicacidal activity. They showed, that the C14 fragment and other fragments are at best as active against C. albicans as the native histatin-5, several of the other fragments being less active. The N16 fragment, for example, was far less active than the C14 fragment.

SUMMARY OF THE INVENTION

Surprisingly, we have now found that the anti-microbial activity of histatins or their fragments can be significantly enhanced by capping them at the C-terminus or at the C- and N-terminus and/or complexing them with anti-microbially-active metal ions. The thus modified histatins and histatin fragments were found to have a significantly increased activity against a range of microbial strains, and were found to be useful as controlled delivery agents for the metal ions, They are suitable for a whole range of anti-microbial applications, such as anti-plaque, anti-caries, anti-bad breath oral applications, deodorant applications, personal hygiene applications and so on, for which they are included in any suitable earlier medium.

DETAILED DESCRIPTION OF THE INVENTION

The histatin to be used according to the present invention for complexing with a metal ion can be any of the known histatins. Preferred are histatin-1, -3 and -5, and of these histatin-5 is particularly preferred. They can be complexed with any of the well-known anti-microbial metal ions such as Ag, Zn, Hg, As, Cu, Pt, Sb, Au, Tl, Ni, Se, Bi, Cd and Sn; preferred metal ions are Ag, Cu, Zn and Sn. The complexing can be carried out in any convenient manner, e.g. using the method as described in WO-A-91/16066 (Berkowitz et al.).

The histatin fragments to be used in the present invention for capping and/or complexing can be any of the known histatin fragments. Preferred are known histatin-5 fragments, and of these C14 fragment is particularly preferred.

The fragments can be complexed as such with the same metal ions in the same manner as described above for the histatins, or they can be capped at the C-terminus or at the C- and N-terminus with suitable capping agents to provide a C-terminal carboxamide group and an N-terminal acyl group. This capping can be carried out in any suitable known manner, e.g. as described by Rink in Tet. Litt. 28 (1987), pages 3787–3790 and by Shoemaker et al. in Nature 326 (1987) pages 563–367.

Typical examples of suitable capping agents are described in Nature 326 (1987), p 563. Examples of acyl groups are acetyl, maleyl, itaconyl, aconityl, citraconyl, citryl and succinyl groups. The preferred acyl groups are acetyl and succinyl groups. These capped histatin fragments can also be complexed with the same metal ions in the same manner as described above for the histatins. Particularly preferred are the capped C14 fragments, which have also been complexed with a metal ion, preferably Ag, Cu, Zn or Sn.

The histatins or fragments thereof, used in the present invention, can be obtained from human saliva, or can be synthesized. The latter is preferred, as the former is intricate and laborious. The compounds of the present invention, which will hereinafter for brevity's sake be referred to as "histatin derivatives" have utility as anti-microbial agents in a wide range of applications.

Mixtures of various histatin derivatives can also be used according to the invention. They are usually used in an mount of 0.01 to 5%, preferably 0.01 to 1% and particularly preferably 0.05 to 0.5%, especially 0.05 to 0.2%. A particularly preferred application is the oral care application, i.e. compositions for the oral care.

The oral compositions can be formulated in any suitable application form, such as emulsions, gels, mouthwashes, toothpowders and toothpaste. They may be formulated into a single formulation or they may be formulated for multi compartment containers into different formulations.

The oral care compositions may, furthermore, comprise optional, conventional ingredients such as pharmaceutically acceptable carriers like starch, sucrose, water or water/alcohol systems etc.. Small amounts of surfactants may also be included, such as anionic, nonionic anti amphoteric surfactants. When formulated into a dentifrice, such formulation may contain all the usual dentifrice ingredients.

Thus, they may comprise particulate abrasive materials including agglomerated particulate abrasive materials such as silicas, aluminas, calcium carbonates, dicalciumphosphates, calcium pyrophosphates, hydroxyapatites, trimetaphosphates, insoluble hexametaphosphates and so on, usually in amounts between 5 and 60% by weight.

Furthermore, the dentifrice formulations may comprise humectants such as glycerol, sorbitol, propyleneglycol, polyethyleneglycol, xylitol, lactitol and so on.

Binders and thickeners such as sodium carboxymethylcellulose, xanthan gum, gum arabic etc. may also be included, as well as synthetic polymers such as polyacrylates and carboxyvinyl polymers such as Carbopol®.

Flavours such as peppermint and spearmint oils may also be included, as well as preservatives, opacifying agents, colouring agents, pH-adjusting agents, sweetening agents and so on.

Other anti-bacterial agents may also be included such as Triclosan, chlorhexidine, copper-, zinc- and stannous salts such as zinc citrate, sodium zinc citrate and stannous pyrophosphate, sanguinarine extract, metronidazole. Further examples of additional anti-bacterial agents are quaternary ammonium compounds such as cetylpyridinium chloride; bis-guanides such as chlorhexidine digluconate, hexetidine, octenidine, alexidine; halogenated bisphenolic compounds such as 2,2'-methylenebis-(4-chloro-6-bromophenol).

Polymeric compounds which can enhance the delivery of active ingredients such as anti-bacterial agents can also be included. Examples of such polymers are copolymers of polyvinylmethylether with maleic anhydride and other similar delivery enhancing polymers, e.g. those described in DE-A-3,942,643 (Colgate)

Furthermore anti-inflammatory agents such as ibuprofen, flurbiprofen, aspirin, indomethacin etc. may aim be included.

Anti-caries agents such as sodium- and stannous fluoride, aminefluorides, monosodiumfluorophosphate, casein, plaque buffers such as urea, calcium lactate, calcium glycerophosphate, strontium polyacrylates may also be included. Other optional ingredients include vitamins such as Vitamin C, and plant extracts. Desensitising agents such as potassium citrate, potassium chloride, potasium tartrate, potassium bicarbonate, potassium oxalate, potassium nitrate as well as strontium salts may also be included.

Buffers and salts to buffer the pH and ionic strength of the compositions may also be included. Liposomes and other encapsulates may also be used to improve delivery or stability of active ingredients.

The histatin derivatives may also be adsorbed onto any suitable particulate material, e.g. an abrasive particulate material, which may then be incorporated into the oral composition.

Furthermore, the oral compositions may comprise anti-calculus agents such as alkalimetal pyrophosphates, hypophosphite-containing polymers, organic phosphonates, phosphocitrates etc..

In addition, the compositions may comprise functional biomolecules such as bacteriocins, antibodies, enzymes and so on.

Other optional ingredients that may be included are e.g. bleaching agents, e.g. those described in EP-A-0 545,594, organic peroxyacids, effervescing systems such as sodium bicarbonate/citric acid systems, colour change systems, and so on.

When formulated as a mouthwash, the oral care composition usually comprises a water/alcohol solution, flavour, humectant, sweetener and colorant.

The present invention win further be illustrated by way of Example.

EXAMPLE 1

Histatin-5 and C14 fragment thereof were synthesized as follows:

All peptides were assembled using a Millipore 9050 fully-automated Peptide Synthesizer using the FMOC solid phase chemistry[1] and Polyhipe solid phase[2].

The individual coupling reactions were monitored by counter-ion distribution monitoring (CDM)[3] and the instrument programmed to re-couple if coupling efficiency registered below 95%. The FMOC-amino acids used were purchased and used directly in the pentafluorophenol ester form (i.e. pre-activated) from Nova-biochem (Nottingham, UK), as were the Polyhipe supports. General reagents and solvents were obtained from Aldrich and used without further purification.

Histatin-5 and the C14 fragment were initially synthesized on a Polyhipe SU500 support functionalised with a hydroxymethylphenoxy acetic acid linker. The first amino acid (Tyr) was attached to the support by esterification of FMOC-Tyr($^1$Bu)-OPfp to the hydroxyl goups in the presence of dimethylaminopyridine as a catalyst. Deprotection (FMOC removal) was effected by piperidine (20% in DMF) and the cycle continued by reaction of the liberated amino groups with FMOC-Gly-OPfp in the presence of HOBt as a catalyst. The deprotection and coupling cycles were repeated, using the appropriate amino acid derivative, until the desired sequence was assembled on the support. Following final FMOC removal the peptides were detached from the linker by reaction with trifluoroacetic acid (TFA), which liberates the free peptide with a C-terminal carboxyl group.

Two further derivatives of the C14 peptide were produced, one with a carboxamide at the C-terminus and a further one with both a C-terminal carboxamide and an N-terminal acetyl group.

To produce the amides the supports were initially functionalised with Rink linker[4], an FMOC protected trialkoxy-benzhydryl type handle, which following removal of the protecting group provides an amine, which simplifies attachment of the first amino acid requiring the same chemistry as for peptide assembly. On cleavage with TFA fragmentation of the linker produces an smite C-terminal group. To incorporate the acetyl-group, acetic anhydride was added as a final residue. The work-up procedure for all peptides was identical, removal of TFA under reduced pressure and trituration and crystallisation of the product using diethyl ether.

A zinc complex of the acetyl-C14-amide was prepared as follows:

The acetyl-$C_{14}$-amide (50 mg, 0.03 mmol) was dissolved in deionised water (200 cm$^3$). The pH of the solution was adjusted to 10 using dilute NaOH solution. Zinc acetate.$2H_2O$ (7 mg, 0.03 mmol) was added and the pH of the solution maintained at 10 by further addition of dilute NaOH solution. The mixture was stirred at room temperature for 2 hours prior to removal of water by freeze drying.

The minimum inhibitory concentrations (MICs) of these peptides were determined as follows:

Organisms were subcultured from BHIS agar into BHI broth and incubated at 37° C. for 2 days. They were then diluted 1/100 in fresh broth and flooded onto pre-dried SDM agar plates. Excess culture was removed by pipetting. Plates were then allowed to dry at room temperature. The various synthesised peptides were dissolved in sterile water at a concentration of 1%. Doubling dilutions, in water, were carried out down to 0.03%. 15 μl of each dilution was spotted onto the lawned cultures, allowed to dry and then the plates were incubated at 37° C. for 2 days. Plates were then read for zones of inhibition. The MIC was taken as the lowest dilution still causing visible growth inhibition.

All organisms were routinely grown on supplemented Brain Heart Infusion agar (Difco) and when appropriate subcultured into Brain Hearth Infusion broth (Difco). For MIC assays a chemically defined solid medium (SDM) was used[5].

The organisms used were the following:

*Streptococcus mutans* strains were clinical isolates, from the plaque of panellists in oral ecology studies. SM11060 (NCTC 11060) and SM10919 (NCTC 10919) were strains obtained from the National Collection of Typed Cultures. SM11060 belonged to serotype f and SM10919 belonged to serotype g. Strain SMB13 (serotype d) was supplied by PHLS, Porton Down.

*Streptococcus sanguis* strains were all clinical isolates from the plaque of panellists in ongoing oral ecology studies.

Actinomyces 12/2, 69A and 41A were plaque isolates from oral ecology studies.

*Steptococcus salivarius* strans were all wild plaque isolates from oral ecology studies.

Lactobacilli were from the in house Colworth Microbial Culture Collection, SB115 and SB116 were *L. casei* var. *rhamnosus*, SB82 had been classified as *L. plantarum*, SB83 and SB85 were *Lactobacillus sp.* and SB 9 was *L. casei*.

Candida strains 83 and 41 were isolated from oral ecology studies. Strains 3091 and 3117 of *Candida albicans* were obtained from the National Collection of Typed Cultures.

Tables 1–3 represent the MiCs measured.

TABLE 1

MICs of Chemically Synthesised Histatin-5 to Oral Micro-organisms

| | Strain | MIC (%) |
|---|---|---|
| S. mutans | SM148dg | 0.5 |
| | SM6715 | 0.5 |
| | SM10449 | 0.25 |
| | SMNW10 | 0.5 |
| | SM84C | 1.0 |
| | SMNW1 | 1.0 |
| | SM44A | 0.5 |
| | SM28B | 1.0 |
| | SMNW6 | 1.0 |
| | SM211 | 0.25 |
| | SM24dg | 1.0 |
| | SM1dg | 1.0 |
| | SM189 | 0.5 |
| S. sanguis | 6/9 | growth stimulated |
| | SS209 | growth stimulated |
| | 10/23 | growth stimulated |
| Lactobacillis | SB9 | 1.0 |
| | SB116 | 1.5 |
| | SB82 | 0.125 |
| | SB81 | 0.125 |
| S. sativarius | 14/9 | growth stimulated |
| | 2/27 | growth stimulated |
| | 2/7 | growth stimulated |
| Actinomyces | 16A | growth stimulated |
| | 11A | 0.5 |
| | 10A | 1.0 |
| | 41A | 1.0 |
| | 69A | growth stimulated |
| | 71A | 0.5 |
| Candida | 83 | >1.0 |
| | 41 | >1.0 |

TABLE 2

MICs Of Short Chain Peptide Fragments to Oral Micro-organisms

| | | MICs (%) | | |
|---|---|---|---|---|
| | Strain | Fragment A | Fragment B | Fragment C |
| S. mutans | SM211 | 0.25 | 0.25 | 0.125 |
| | SM11060 | 0.5 | 0.5 | 0.25 |
| | SMNN6 | 0.5 | 1.0 | 0.25 |
| | SM28B | 1.0 | 1.0 | 0.5 |
| | SM189 | 1.0 | >1.0 | 0.5 |
| | SM10C | 1.0 | 1.0 | 0.25 |
| | SM148dg | 0.5 | 0.5 | 0.25 |
| | SMN13 | 0.5 | 0.5 | 0.25 |
| | SM31dg | 0.5 | 0.5 | 0.25 |
| | SM24dg | 0.5 | 0.5 | 0.25 |
| | SM152C | 0.25 | 0.25 | 0.125 |
| | SM166dg | 0.5 | 0.5 | 0.25 |
| | SMNW1 | 0.25 | 0.5 | 0.125 |
| | SM10919 | 0.5 | 0.5 | 0.25 |
| S. sanguis | SS209 | >1.0 | >1.0 | >1.0 |
| | SS3 | >1.0 | >1.0 | 0.5 |
| | 6/11 | >1.0 | 0.5 | 0.5 |
| | 6/9 | >1.0 | >1.0 | 0.5 |
| | 10/23 | >1.0 | 0.5 | 0.5 |
| S. salivarius | 4/14 | >1.0 | >1.0 | 0.5 |
| | 14/19 | 0.5 | 0.25 | 0.125 |
| | 2/27 | 1.0 | 0.5 | 0.125 |
| | 4/2 | 1.0 | 0.5 | 0.125 |
| Lactobacilli | SB85 | 1.0 | 1.0 | 0.25 |
| | SB83 | 0.5 | 0.25 | 0.25 |
| | SB115 | 1.0 | 1.0 | 0.5 |
| | SB82 | 0.5 | 0.5 | 0.06 |
| | SB9 | >1.0 | >1.0 | 0.25 |
| | SB116 | 1.0 | 1.0 | 0.25 |
| Antinomyces | 12/2 | >1.0 | 0.5 | 0.25 |
| | 69A | >1.0 | 0.125 | 1.125 |
| | 41A | >1.0 | 0.5 | 0.25 |
| | 12104 | >1.0 | >1 | 1.0 |
| Candida | 83 | >1.0 | >1.0 | 0.25 |
| | 41 | >1.0 | >1.0 | 0.125 |
| | 3091 | 0.25 | 0.125 | 0.125 |

A = Fragment C14
B = Fragment C14-amide
C = Fragment acetyl-C14-amide

TABLE 3

MICs of acetyl-C14-amide Containing Zinc to Selected Oral Micro-organisms

| | Strain | MIC (%) |
|---|---|---|
| S. mutans | SM211 | 0.06 |
| | SM10919 | 0.06 |
| | SM10449 | 0.125 |
| | SM11060 | 0.06 |
| S. sanguis | SS3 | 0.125 |
| | SS209 | 0.25 |
| Lactibacillis | SB9 | 0.06 |
| | SB82 | <0.03 |
| | SB116 | 0.06 |
| S. salivarius | 14/9 | <0.03 |
| | 4/2 | <0.03 |
| Actinomyces | 41A | 0.06 |
| | 12104 | 0.06 |
| | A69 | 0.125 |
| Candida | 41 | 0.06 |
| | 83 | 0.06 |
| | 3091 | <0.03 |

References

1. Atherton, E. and Sheppard, R. C. (1989), Solid Phase Synthesis: a practical approach, IRL Press, Oxford 2. Small P. W. and Sherrington, D. C. (1989), J. Chem. Soc. Chem. Commun., 1589.
3. Young, S. C., White, P. D, Davies, J. W., Owen, D. E., Salisbury, S. A., and Tremeer, E. J., (1990), Biochem. Soc. Trans, 18: 1311.
4. Rink, H., (1987), Tet. Lett., 28: 3787.
5. Mackay, B. J., Denepitiya, L., Iacono, V. J., Krost, S. B., and Pollock, J. J. (1984). Inf. and Immun. 44: 695–701.

We claim:

1. An anti-microbial cosmetic composition for the care of the human body, comprising a carrier medium and an effective amount of histatins or their fragments, which have been capped at the C-terminus.

2. A composition according to claim 1, wherein the histatins or their fragments have also been capped at the N-terminus.

3. A composition according to claim 1, wherein the C-terminus capped histatins or their fragments have been complexed with an anti-microbially-active metal ion.

4. A composition according to claim 2, wherein the capped histatins or their fragments have been complexed with an anti-microbially-active metal ion selected from the group consisting of silver, copper, zinc and tin (II).

5. An anti-microbial cosmetic composition for the care of the human body, comprising a carrier medium and an effective amount of histatins or their fragments, which have been complexed with an anti-microbially-active metal ion selected from the group consisting of silver, copper, zinc and tin (II).

6. A composition according to claim 1, wherein the histatin is selected from the group consisting of histatin-1, histatin-3, histatin-5 and a fragment thereof.

7. A composition according to claim 1, wherein the histatin is histatin -5 or a fragment thereof.

8. A composition according to claim 7, wherein the histatin -5 fragment is the C14 fragment.

9. A composition according to claim 1, wherein the histatin fragments have been capped with a C-terminal carboxamide group.

10. A composition according to claim 2, wherein the histatins or their fragments have been capped with an N-terminal acyl group.

11. A composition according to claim 1, wherein the composition is in the form of an oral care composition.

12. A composition according to claim 5, wherein the composition is in the form of an oral care composition.

* * * * *